United States Patent [19]

Hibino et al.

[11] Patent Number: 4,970,157

[45] Date of Patent: Nov. 13, 1990

[54] ISOLATED PHENYLALANINE DEHYDROGENASE GENE AND PROCESS FOR PRODUCTION OF PHENYLALANINE DEHYDROGENASE

[75] Inventors: Yasuo Hibino; Yasuhisa Asano, both of Sagamihara, Japan; Noriko Okazaki, Rockville, Md.; Naganori Numao, Sagamihara, Japan

[73] Assignees: Sagami Chemical Research Center; Central Glass Company, Limited; Hodogaya Chemical Co., Ltd.; Nippon Soda Company, Limited; Nissan Chemical Industries, Limited; Toyo Soda Manufacturing Co., Ltd., all of Japan

[21] Appl. No.: 84,238

[22] Filed: Aug. 11, 1987

[30] Foreign Application Priority Data

Aug. 12, 1986 [JP] Japan ................................ 61-187852
Nov. 27, 1986 [JP] Japan ................................ 61-280654

[51] Int. Cl.$^5$ ...................... C12N 9/02; C12N 15/00; C12N 1/20
[52] U.S. Cl. ................................ 435/189; 435/252.3; 435/252.31; 435/252.33; 435/320; 435/108; 435/172.3; 536/27; 935/1; 935/29; 935/73; 935/74
[58] Field of Search .................. 435/172.3, 108, 252.3, 435/252.33, 320, 189; 536/27

[56] References Cited

U.S. PATENT DOCUMENTS 4,590,161  5/1986  Kula et al. ......................... 435/113

FOREIGN PATENT DOCUMENTS 0137646   4/1985   European Pat. Off. .
206460   12/1986   European Pat. Off. .
206904   12/1986   European Pat. Off. .
212972    3/1987   European Pat. Off. .
59-198972 11/1984  Japan .
60-24192   2/1985  Japan .
60-66984   4/1985  Japan .
60-160890  8/1985  Japan .
60-164493  8/1985  Japan .
2053906    2/1981  United Kingdom .

OTHER PUBLICATIONS

Asano, et al., *Eur. J. Biochem.* 168:153–150, 1987.
Asano, et al., *Agric. Biol. Chem.* 51(9):2621–2623, 1987.
Patent Abstracts of Japan, vol. 9, No. 138 (C-286) (1861), Jun. 13, 1985, JP 60-24192(A).
Ozaki et al., "Cloning and Nucleotide Sequencing of Phenylalanine Dehydrogenase Gene of *Bacillus sphaericus*", *Gene*, vol. 63, No. 2, pp. 337–341 (1988)
Asano et al., "Novel Phenylalanine Dehydrogenases from *Sporosarcina ureae* and *Bacillus sphaericus*," The *Journal of Biological Chemistry*, vol. 262, No. 21, pp. 10346–10354, Jul. 25, 1987.

*Primary Examiner*—Robin L. Teskin
*Assistant Examiner*—Beth A. Burrous
*Attorney, Agent, or Firm*—Wegner & Bretschneider

[57] ABSTRACT

An isolated gene coding for phenylalanine dehydrogenase of a microorganism belonging to a genus selected from the group consisting of the genera Bacillus and Sporosarcina origin; plasmids containing the gene; microorganism transformed with the plasmid, a process for the production of phenylalanine dehydrogenase using the microogranism; and a process for the production of L-phenylalanine using the enzyme.

8 Claims, 10 Drawing Sheets

Fig. 3-1

```
                                                                                         GGCCTGATCGGTTCCGGTTAT
TCGTGAATGCGGATAAGAAATCCTTACGTGCCATCCATCAAGAAATGAAGGAATTGACACAAAGGCAAAAGAGAACAAG
CTGGCAGTGCGTGAAATCACAGGCAGCACTTTTACAATCAGCAACGTTGGTCCTAAGGAAGCATTGGCGCAACACCGAT
CATCAATTATCCTGAAACAGGGCTTATGGCATTCCATAAAACGAAAAAGATGCCTGTCGTCAATGAGCACGATGAAAGCG
GTATTCGTTCCATGATGAACGTGACAATGACGTTTGACCATCGTCGCCGACGGTGAACAGTCAATTGCTTTTACAAA
CCGATTTAAATCCTTGAATTGAAGATCCCAAAAAATTAATGCTGGAGCTTGTCTGATAAGATTGAATGGAGGAAAAGAA
          10        20        30         40        50        60       70        80
ATGGCAAAACAGCTTGAAAAGTCATCAAAAATTGGTAATGAGGACGTTTTCAAAAATAGCGAATCACGAGCAGATTGT
 A  K  Q  L  E  K  S  S  K  I  G  N  E  D  V  F  Q  K  I  A  N  H  E  Q  I  V
          90       100       110        120       130       140      150       160
GTTCTGTAATGATCCGGTATCCGGCTGCAAGCTATCATTGCTATCCACGATACAACCCTAGGCCCCGCTTTAGGTGAA
 F  C  N  D  P  V  S  G  L  Q  A  I  I  A  I  H  D  T  T  L  G  P  A  L  G  G  T
          170      180       190        200       210       220      230       240
CTCGCAATGTATCCCTATAAAAATGTGGATGAAGCTCTGGAAGATGTGCTTCGCCTGTCAGAAGAATGACGTATAAATGC
 R  M  Y  P  Y  K  N  V  D  E  A  L  E  D  V  L  R  L  S  E  G  M  T  Y  K  C
          250      260       270        280       290       300      310       320
GCAGCCGCCGATATCGATTTCGGCGGCGGAAGGCGGTCATTATCGGAGATCCAGAAAAGGATAAATCTCCGGCATTGTT
 A  A  D  I  D  F  G  G  G  K  A  V  I  I  G  D  P  E  K  D  K  S  P  A  L  F
```

Fig. 3-2

```
          330         340         350         360         370         380         390         400
CCGTGCATTTGGTCAATTTGTGGAATCACTGAATGGACGATTTTACACAGTACTGACATGGGGACCACGATGGATGATT
 R   A   F   G   Q   F   V   E   S   L   N   G   R   F   Y   T   G   T   D   M   G   T   T   M   D   D   F 410         420         430         440         450         460         470         480
TTGTCCATGCACAGAAAGAGACGAATTTCATTAACGGAATTCCTGAGCAGTATGGTGGAAGCGGCGACTCGTCGATTCCG
 V   H   A   Q   K   E   T   N   F   I   N   G   I   P   E   Q   Y   G   G   S   G   D   S   S   I   P 490         500         510         520         530         540         550         560
ACCGCCCAGGGAGTCATTTATGCACTGAAGGCTACAAACCAGTATTTATTTGGAAGCGATAGCCTTTCAGGTAAAACATA
 T   A   Q   G   V   I   Y   A   L   K   A   T   N   Q   Y   L   F   G   S   D   S   L   S   G   K   T   Y 570         580         590         600         610         620         630         640
TGCTATTCAAGGGCTGGGAAAAGTAGGGTATAAAGCGGAACAGCTCTTAAAAGCCGGCGCCGATTTATTTGTAACGG
 A   I   Q   G   L   G   K   V   G   Y   K   V   A   E   Q   L   L   K   A   G   A   D   L   F   V   V   D 650         660         670         680         690         700         710         720
ATATACATGAAAATGTCCTCAATTCCATTAAGCAAAAATCAGAAGAGCTTGGCGGTTCAGTGACCATTGTAAAAAGTGAC
 I   H   E   N   V   L   N   S   I   K   Q   K   S   E   E   L   G   G   S   V   T   I   V   K   S   D 730         740         750         760         770         780         790         800
GATATTTACAGCGTACAAGCGGATATATTTGTTCCGTGTGCCGATGGGTGGTATTATCAATGATAAAACCATTCCTAAGTT
 D   I   Y   S   V   Q   A   D   I   F   V   P   C   A   M   G   G   I   N   D   K   T   I   P   K   L 810         820         830         840         850         860         870         880
AAAGGTGAAGGCTGTGTTGTGGGATCAGCCAATAACCAGCTCAAAGACCTCCGCCATGCAAATGTACTAAACGAAAAGGAA
 K   V   K   A   V   V   G   S   A   N   N   Q   L   K   D   L   R   H   A   N   V   L   N   E   K   G   I
```

Fig. 3-3

```
         890       900       910       920       930       940       950       960
TTCTATATGCACCCGATTATATCGTCAATGCCGGCGCTTGATCCAGGTTGCTGACGAACTTTATGGGCCGAATAAAGAG
 L  Y  A  P  D  Y  I  V  N  A  G  G  L  I  Q  V  A  D  E  L  Y  G  P  N  K  E 970       980       990      1000      1010      1020      1030      1040
CGGGTCTTGCTCAAAACGAAAGAAATTTACCGTTCTCTGCTTGAAATTTTAATCAGGCAGCCCTTGACTGCATCACAAC
 R  V  L  L  K  T  K  E  I  Y  R  S  L  L  E  I  F  N  Q  A  A  L  D  C  I  T  T 1050      1060      1070      1080      1090      1100      1110      1120
AGTGGAGGCCCGCAAATAGGAAGTGTCAAAAGACGATTGAGGGCCAGCAAACCCGTAATAGTTTCTTTTCTAGGGACGCA
 V  E  A  A  N  R  K  C  Q  K  T  I  E  G  Q  Q  T  R  N  S  F  F  S  R  G  R  R 1130      1140
GGCCGAAGTGGAACATAAAAGAGTAATATTGAAAGCGTAAACATTGAAGAGAGCTGAACATATGAACAAATATGAAAC
 P  K  W  N  I  K  E  *

GATTGATCTTATGGAGGTGGCCACTCCTCCCAAATTGTGATCTTACCTTGCAAATCCAGCCTGTTCATG
CAAAGGATGGAAAATCAAAAGGAATTTGGAGGTAGATGAGAGAAATTCCTGAATGGGCTTGGTGTCACAATGGGCGATAC
```

```
                                          ACTTTTTAGTAAGTAATATTCTCATGGCCACTCGGTGCCGTTGTTGATCGCTCTATTCAT
CCCACTAAAAATACCGAAAGAAAAGCTCTATGAAGAATTGAAGGCCGGCTCCAATATCAGCACACAATTATTTCTGC
CTGCCTGGTTTTTATTAATTCGTTACCTTGCACCGGTAGCTATTCTCATGCGTGTATTGCAGACGTACTTGGACTATT
GAACTTCTTGAAATAAATAGATAGATTGCTGATACCCTCATATAGGTTCACAGCAATAAAATAGAGGAGAAATGATT
                10        20        30        40        50        60        70        80
TTGGTAACTTTAGAACAGACTTTACAAGACGACAAGGCAAGTGTTTTGGATAAAATGGTCGAGCATGAACAAATTCTA
 V  T  L  E  Q  T  L  Q  D  D  K  A  S  V  L  D  K  M  V  E  H  E  Q  I  L
      88        98       108       118       128       138       148       158
TTTGTCATGATAAAGCAACCGGTCTTCAAGCCATCATTGCAGTCCACGATACGACTATGGGACCTGCACTCGGTGGAT
 F  V  M  I  K  Q  P  V  F  K  P  S  L  Q  S  T  I  R  L  W  D  L  H  S  V  D
     166       176       186       196       206       216       226       236
GTGTCCATGGCGCCTTATAAAACGATGGATCTCGCATTAAAAGATGTTCTTCGCCTTCAAAAGGGATGACATATAAAA
 V  S  M  A  P  Y  K  T  M  D  L  A  L  K  D  V  L  R  L  S  K  G  M  T  Y  K
     244       254       264       274       284       294       304       314
TGTGCGGCAGCTGATGTAGACTTTGGCGGCGGAAAATCCGTCATCATCGGAGACCCGCTAAAAGATAAACGCCTGAG
 C  A  A  D  V  D  F  G  G  G  K  S  V  I  I  G  D  P  L  K  D  K  T  P  E
     322       332       342       352       362       372       382       392
AAATTCCGTGCTTTCGGTCAATTCATCGAATCATTGAACGGACGCTTCTATACAGGTACAGACATGGGCACAACGCTT
 K  F  R  A  F  G  Q  F  I  E  S  L  N  G  R  F  Y  T  G  T  D  M  G  T  T  L
```

Fig. 5-2

```
        400       410       420       430       440       450       460       470
GAAGACTTTGTGCATGCCATGAAAGAAACAAACTACATCGTGGCAAGCCGGTCGAATATGGTGGCGGTGGAGACTCAT
 E  D  F  V  H  A  M  K  E  T  N  Y  I  V  A  S  R  S  N  M  V  A  V  E  T  H 478       488       498       508       518       528       538       548
CGATCCCTACTGCACTCGGAGTCTTCTATGGCATTAAAGCGACAAACCATGAATCTGTTTGGCGACGACAAAGTAGAA
 R  S  L  L  H  S  E  S  S  M  A  L  K  R  Q  T  M  N  L  F  G  D  D  K  V  E 556       566       576       586       596       606       616       626
GGCCGAAAATACAGTATCCAAGGTCTTGCGAAAGTAGGTTACAAAGTAGCTGAACATATTATCAACGAAGGTGGAAAG
 G  R  K  Y  S  I  Q  G  L  A  K  V  G  Y  K  V  A  E  H  I  I  N  E  G  G  K 634       644       654       664       674       684       694       704
CTGATGCTCACAGATATTAATGAGCAAGCGATTGCAGATATTCAGAAGCTCGGTGGAAGCGCTGTCAGGGTCGTATCA
 L  M  L  T  D  I  N  E  Q  A  I  A  D  I  Q  K  L  G  G  S  A  V  R  V  V  S 712       722       732       742       752       762       772       782
AGTGAGGAGATTTACAGTCAGCAAGTCAAGTGTTTTTGTTCCTTGTGCATTTGGTCGCGTGATCAATAGACGACACGCT
 S  E  E  I  Y  S  Q  Q  A  S  V  F  V  P  C  A  F  G  R  V  I  N  R  R  H  A 790       800       810       820       830       840       850       860
AAAGGTCTGAAAGTACGAGGAATCTCCGGTTCAGCAAACAATCAGCTCGGAAGCCGCCATGGAGAGCTACTACGTGAA
 K  G  L  K  V  R  G  I  S  G  S  A  N  N  Q  L  G  S  R  H  G  E  L  L  R  E 868       878       888       898       908       918       928       938
AAGGGTATTTTGTACGCACCAGACTATATCGTCAACGGGCGGGTTTAATCCAAGTGGCGGATGAATTGTACGGAACG
 K  G  I  L  Y  A  P  D  Y  I  V  N  G  G  L  I  Q  V  A  D  E  L  Y  G  T
```

Fig. 5-3

```
     946        956        966        976        986        996       1006       1016
AATCCTGCACGTGTACTCGCTAAAACTGAAAACATCTATACCTCACTGCTTGAAGTATTCCATCAGGCAGAACAGGAT
 N  P  A  R  V  L  A  K  T  E  N  I  Y  T  S  L  L  E  V  F  H  Q  A  E  Q  D 1024       1034       1044       1054       1064       1074       1084       1094
CATATGACAACTGCCACTGCCGCAGACCGTATGTGTGAAAAGCGTATTGCGGATGCCAAGAATCGCAACAGCTTCTTC
 H  M  T  T  A  T  A  A  D  R  M  C  E  K  R  I  A  D  A  K  N  R  N  S  F  F 1102       1112       1122       1132
ACACAGTCAAACCGACCGAAATGGAATTTCATCAGTAATAAAAATAGCTGAATGAGGTGATGAATT
 T  Q  S  N  R  P  K  W  N  F  H  Q  *  *
```

ISOLATED PHENYLALANINE DEHYDROGENASE GENE AND PROCESS FOR PRODUCTION OF PHENYLALANINE DEHYDROGENASE

BACKGROUND OF THE INVENTION

1. Field of the Invention

The present invention relates to genes coding for phenylalanine dehydrogenase, plasmids containing the gene, microorganisms transformed with the plasmid, a process for the production of phenylalanine dehydrogenase, and a process for the production of L-phenylalanine using an enzyme.

2. Description of the Related Art

Attempts have been made to produce L-amino acids using α-ketocarboxylic acid as a substrate. For example, a process for preparing L-glutamic acid by adding α-ketoglutarate and various kinds of amino acids to microbial cells (Katagiri et. al. *Amino Acid and Nucleic Acid*, 2, 18, 1960); a process for obtaining L-phenylalanine by adding L-glutamic acid or L-aspartic acid to a reaction mixture containing phenylpyruvic acid (Asai et. al., *Amino Acid and Nucleic Acid*, 2, 114 (1960); and a process for synthesizing L-tryptophan by adding L-glutamic acid or L-aspartic acid to a reaction mixture containing indolepyruvic acid (Aida et. al., *Journal of General and Applied Microbiology*, 4, 200, 1958, have been disclosed.

Japanese Unexamined Patent Publication No. 60-164493 describes a process for the production of L-phenylalanine by either culturing one of various kinds of microorganisms with phenylpyruvic acid and an amino group donor, or incubating cells of that microorganism or a treated product of the cells with phenylpyruvic acid and an amino group donor. However, this specification does not disclose just what kind of enzymes participate in the reaction. Moreover, such processes employ amino acids, which are an expensive amino group donor.

All of the above-mentioned processes use, as an amino group donor of an aimed amino acid, another amino acid, and are fundamentally different from a process of the present invention which uses an ammonium ion as an amino group donor, which is not so expensive. Namely, the prior art processes are more expensive than the present process. Moreover, the enzymes involved in the prior art process are different from those of the present process.

Japanese Unexamined Patent Publication No. 60-43391 discloses a process for production of L-amino acid wherein a microorganism capable of converting an α-keto acid to a corresponding L-amino acid is cultured, and during the culturing, the α-keto acid is fed into the culturing medium to convert the α-keto acid to the L-amino acid. According to the reaction mechanism suggested in the specification, as an amino group donor for the formation of an aimed L-amino acid from a corresponding α-keto acid, L-glutamate is used, which means that the reaction is carried out by an amino transferase. Moreover, the application discloses only Brevibacterium, Corynebacterium, and *Escherichia coli* as microorganisms involved.

Japanese Unexamined Patent Publication No. 59-198972 describes phenylalanine dehydrogenase and a process for the production of L-α-amino carboxylic acid using that enzyme. However, the phenylalanine dehydrogenase described therein is derived from Brevibacterium, and the specification does not suggest that Sporosarcina and Bacillus produce a similar enzyme. Moreover, the disclosed phenylalanine dehydrogenase has a molecular weight of 130,000±10,000 and consists of subunits having a molecular weight of 66,000±5,000 and, therefore, is different from the present phenylalanine dehydrogenase.

Japanese Unexamined Patent Publication No. 60-160890 discloses a process for the production of L-phenylalanine by either culturing one of various kinds of microorganisms with phenylpyruvate in the presence of an energy source, an inorganic ammonium compound or urea, and oxygen, or by incubating a cultured product of the microorganism or treated product thereof with phenylpyruvate in the presence of an energy source, an inorganic ammonium compound or urea, and oxygen. However, the specification does not suggest the kind of enzymes involved in the process, and the process is supposed to be essentially a fermentation process, due to the necessity for the presence of oxygen. Moreover, the specification does not refer to Sporosarcina.

Japanese Unexamined Patent Publication No. 60-24192 discloses the production of L-phenylalanine using a Corynebacterium strain transformed with a plasmid containing genes related to L-phenylalanine production derived from Corynebacterium.

Japanese Unexamined Patent Publication No. 60-62992 discloses the cloning of genes related to the synthesis of L-phenylalanine in *Escherichia coli*, and the expression of that gene under the control of a trp promoter to produce L-phenylalanine.

Japanese Unexamined Patent Publication Nos. 60-66984 and 60-210993 disclose the synthesis of L-phenylalanine using Brevibacterium microorganism transformed with a plasmid incorporating a gene for an enzyme related to L-phenylalanine synthesis, which gene is from L-glutamate-producing Coryneform. phenylalanine dehydrogenase genes of Bacillus and Sporosarcina origin, plasmids containing that gene, microorganisms transformed with the plasmid, and a process for the production of L-phenylalanine have not been described.

Note, microorganism producing phenylalanine dehydrogenase, a process for production of phenylalanine dehydrogenase, phenylalanine dehydrogenase per se, and a process for production of α-amino acid including L-phenylalanine are described in detail in E.P.C publication No. 0 206 460.

Generally, the ability of wild microorganism strains to produce useful substances is low, and therefore, when the production of useful substances is intended, using a microorganism, an improvement of microorganism is attempted to increase the ability of the microorganism to produce a target substance. However, conventional processes for the improvement of a microorganism, such as artificial mutagenesis using, for example, a chemical mutagen or physical mutagen such as UV rays, are time-consuming and depend greatly on chance.

SUMMARY OF THE INVENTION

Accordingly, in the present invention, a gene technology is used to enhance the ability of microorganisms to produce phenylalanine dehydrogenase.

The present invention provides an isolated gene coding for phenylalanine dehydrogenase of a microorganism belonging to the genus selected from the group consisting of the genera Bacillus and Sporosarcina origin.

The present invention also provides expression plasmids containing the above-mentioned genes.

The present invention also provides microorganisms transformed with the above plasmids.

The present invention also provides a process for the production of an phenylalanine dehydrogenase comprising the steps of:
 culturing the above-mentioned microorganism, and
 recovering the phenylalanine dehydrogenase from the cultured product.

The present invention further provides, a process for the production of an L-phenylalanine comprising the steps of:
 reacting phenylpyruvic acid or a salt thereof with ammonium ion in an aqueous medium in the presence of the phenylalanine dehydrogenase produced by the above-mentioned process and a reducing agent to form L-phenylalanine, and
 recovering the L-phenylalanine

BRIEF DESCRIPTION OF THE DRAWINGS

FIGS. 3-1 to 3-3 represent a nucleotide sequence (upper line) of a DNA fragment in the plasmid pBPDH1 containing a region coding for the present phenylalanine dehydrogenase, and an amino acid sequence (lower line) corresponding to the above-mentioned nucleotide sequence;

FIGS. 5-1 to 5-3 represent a nucleotide sequence (upper line) of a DNA fragment in the plasmid pSPDH1 containing a region coding for the present phenylalanine dehydrogenase, and an amino acid sequence (lower line) corresponding to the above-mentioned nucleotide sequence.

DESCRIPTION OF THE PREFERRED EMBODIMENT

Figure 1:
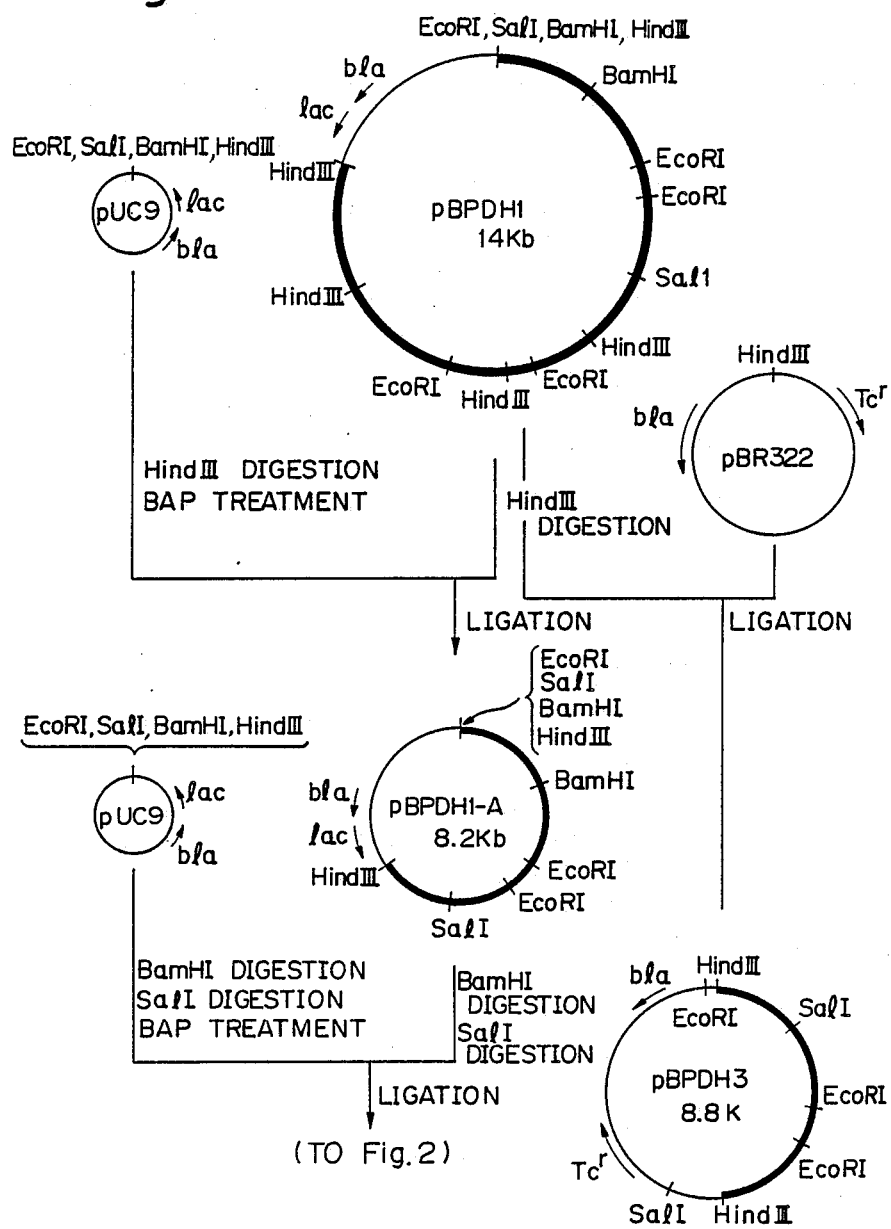
FIGS. 1 and 2 represent a process for the construction of plasmids pBPDH3, pBPDH1-DBL, and pBPDH1-DBR from a plasmid pBPDH1, all containing an phenylalanine dehydrogenase gene.

According to the present invention, DNA is extracted from a microorganism belonging to the genus Bacillus or Sporosarcina and capable of producing phenylalanine dehydrogenase, an phenylalanine dehydrogenase gene is obtained by cleaving the extracted DNA with appropriate restriction enzymes, the gene is introduced to an appropriate vector to construct an expression plasmid, and a microorganism is transformed with the expression plasmid to form an phenylalanine dehydrogenase-producing transformant. This transformed microorganism is used to produce an phenylalanine dehydrogenase, which is then used to produce L-phenylalanine.

1. Microorganism as gene source

Microorganisms which can be used as a gene source for the present invention are those belonging to the genus Sporosarcina or Bacillus and capable of producing phenylalanine dehydrogenase. Such microorganisms may be selected from deposition libraries or may be isolated from natural sources.

The microorganisms belonging to the genus Sporosarcina include Sporosarcina ureae. Such species include, for example, strains Sporosarcina ureae IFO 12698 and Sporosarcina ureae IFO 12699 (ATCC 6473) as species selected from deposition library, and Sporosarcina ureae SCRC-R04 first isolated by the present inventor. The former strains can be obtained from the Institute for Fermentation Osaka (IFO), 17-85 Juso-honmachi 2-chome, Yodogawa-ku, Osaka 532, Japan, or the American Type Culture Collection (ATCC), 12301, Parklawn Drive, Rockville, Md. 20852, U.S.A.; and the latter strain, Sporosarcina ureae SCRC-R04, was deposited with the Fermentation Research Institute Agency of Industrial Science and Technology, Ministry of International Trade and Industry (FRI), 1-1-3 Yatabe-cho Higashi, Tsukuba-gun, Ibaraki-ken, Japan, as FERM P-8178, on Apr. 16, 1985, and transferred to the international deposition under the Budapest Treaty on the International Recognition of the Deposit of Microorganisms for the Purposes of Patent Procedure (Budapest Treaty) as FERM BP-1012 on Apr. 3, 1986.

The microorganisms which can be used as a gene source in the present invention belonging to genus Bacillus include, for example, Bacillus alvei IFO 3343; Bacillus thiaminolyticus IAM 1034 deposited with FRI as FERM P-8528 on Nov. 28, 1986; Bacillus badius IAM 11059, ATCC 14574, deposited with FRI as FERM P-8529 on Nov. 28, 1985; Bacillus sphaericus IFO 12622; Bacillus sphaericus IAM 1228, deposited with FRI as FERM P-8527 on Nov. 28, 1985. All of the above-mentioned strains are listed in catalogs published by IFO, ATCC, or for IAM by the Japanese Federation of Culture Collections of Microorganisms (JFCC), Institute of Medical Science, University of Tokyo, Shiroganedai 4-6-1, Minato-ku, Tokyo 108, Japan, and are available to the public.

Moreover, the microorganism which can be used as a gene source in the present invention includes new strains isolated by present inventors, such as Bacillus sp. SCRC-R53b; Bacillus sp. SCRC-R79a deposited with FRI as FERM P-8179 on Apr. 16, 1985, and transferred to the international deposition under the Budapest Treaty as FERM BP-1013 on Apr. 3, 1986; Bacillus sp. SCRC-101A; and Bacillus sp. SCRC 114D deposited with FRI as the international deposition FERM BP-1011 on Apr. 3, 1986.

According to Bergey's Manual of Determinative Bacteriology, the eighth edition, 1974, the above-listed strains were identified as follows:

(a) SCRC-R04 is aerobic, motile, capable of forming spores, Gram positive, and 2 to 4 cocci. Therefore the strain belongs to genus Sporosarcina. Since Sporosarcina includes Sporosarcina ureae as sole species, and the above-mentioned properties of SCRC-R04 are almost consistent with those described in the literature, the strain SCRC-R04 is identified to be Sporosarcina ureae.

(b) All SCRC-R53b, SCRC-R79a, SCRC-101A and SCRC-114D are Gram positive, rod, capable of forming endospores and forming catalase. Therefore, they belong to Bacillus.

Details of the properties of the above-mentioned strains are described in E.P.C. patent publication No. 0 206 460.

2. Cloning of phenylalanine dehydrogenase gene and construction of expression plasmid According to the present invention, any of the above-mentioned phenylalanine dehydrogenase-producing microorganisms can be used as the gene source, and an embodiments wherein *Bacillus sphaericus* SCRC-R79a (FERM BP-1013) *Sporosarcina ureae* SCRC-R04 (FERM BP-1012) and *Bacillus badius* IAM 11059(FERM P-8529) are used is definitively described herein. The process for gene cloning is described in detail in the Examples.

Although as an expression control region for the present phenylalanine dehydrogenase gene that naturally accompanies the phenylalanine dehydrogenase gene can be used, to enhance the expression or to make possible the induction of the expression, a foreign promoter/operator is preferably used. If *E. coli* is used as a host, trp, tac, lacUV5, $P_L$, $P_R$, lpp or the like may be used as a promoter/operator, and as the SD sequence, that of a trp leader peptide, lacZ, metapyrocatechase gene, cII gene or the like may be used. Moreover, a transcription terminator, such as a rrnBT$_1$, T$_2$ terminator of an *E. coli* ribosome gene can be provided downstream of the coding region. Moreover, for the production of an phenylalanine dehydrogenase gene, a host/vector system of *Saccharomyces cerevisiae* can be used. As the yeast promoter, a promoter of an alcohol dehydrogenase gene, a promoter of an acidic phosphatase gene, a promoter of a glyceraldehyde-3-phosphate dehydrogenase, a promoter of an enolase, or the like, can be used. The yeast plasmid preferably contains a yeast replication origin and a selective maker for a selection of yeast cells containing the plasmid, for example, a gene providing prototrophy to a auxotrophic host such as an LEU, TRP, HIS gene or the like.

Generally, an amount of the expression of a particular protein in yeast cells depends on the copy number of the gene to be expressed, the efficiency of the transcription, the stability of the mRNA, the efficiency of the translation, and the stability of the produced protein. To modify expression control regions such as the promoter, SD sequence, terminator and the like, preferably the plasmid is small. Note, the smaller the plasmid, the greater the increase in the copy number. Therefore, after a DNA fragment containing an phenylalanine dehydrogenase gene is inserted into a plasmid, preferably the subcloning of the plasmid is repeated to eliminate a non-coding region of the DNA fragment and thus reduce the size of the plasmid.

According to the present invention, preferably the host is an *E. coli* strain, for example, a strain derived from *E. coli* K-12, such as JM83, JM101, JM103, JM105, JM109, RR1, RB791, W3110, C600, HB101, DH1 and the like. On the other hand, as the yeast host, preferably *Saccharomyces cerevisiae* strains such as AH22, DC5, D-13-1A, YNN140 and the like are used.

3. Production of phenylalanine dehydrogenase

According to the present invention, phenylalanine dehydrogenase can be produced by a conventional method used for the production of a protein by genetic engineering procedures. For example, a microorganism such as *E. coli*, transformed with an expression plasmid containing phenylalanine dehydrogenase gene, is cultured in an appropriate medium, and when the cell concentration reaches a predetermined level, an induction treatment, which depends on nature of the control region of the plasmid used, is carried out to produce an phenylalanine dehydrogenase.

L-phenylalanine is recovered and purified from the cultured broth according to a combination of conventional procedures used for the purification of an enzyme. For example, a cultured broth is centrifuged to collect bacterial cells. The cells are then disrupted by a conventional method such as ultrasonication or Dynomill treatment, and debris eliminated by a conventional method such as centrifugation or filtration to obtain a supernatant or filtrate containing the aimed enzyme. Further purification, for example, protamine sulfate treatment, streptomycin sulfate treatment, salting out, organic solvent precipitation, absorption chromatography, ion exchange chromatography, gel filtration chromatography, and crystallization using, for example, ammonium sulfate or polyethyleneglycol, may be used.

The activity of the present phenylalanine dehydrogenase is determined according to the following procedures: 100 $\mu$ moles of glycine-KCl-KOH buffer (pH 10.5), 2.5 $\mu$ moles of NAD$^+$, 10 $\mu$ moles of L-phenylalanine, and an appropriate amount of sample are mixed to a total volume of 1 ml to react the components, and the increase of an amount of NADH is measured according to the increase of absorption at 340 nm. An amount of the enzyme which increases an amount of NADH by 1 $\mu$ mole per 1 minute is defined at 1 unit.

4. Production of L-phenylalanine

According to one embodiment of the present process, a phenylpyruvic acid, NADH and ammonium ion are reacted under the presence of phenylalanine dehydrogenase to form L-phenylalanine, and the L-phenylalanine is recovered.

The forms of the enzyme preparations of phenylalanine dehydrogenase are not limited. The preparations include, for example, a completely purified enzyme; cultured broth containing cells; living cells; dried cell powders prepared by treating cells with, for example, acetone or ethanol; disrupted cells; and partially purified enzyme preparations purified to various purification stages. Moreover, immobilized enzyme preparations, such as immobilized enzyme and immobilized enzyme-containing products prepared according to conventional procedures may be used. For industrial production, living cells or immobilized enzyme preparations are preferably used.

An amount in a reaction medium of phenylalanine dehydrogenase derived from the above-mentioned enzyme preparation is not critical, but preferably is within about 10 to 10,000 units per 1 liter, depending on the nature and amount of the substrate α-ketocarboxylic acid and other conditions.

As a substrate, both phenylpyruvic acid and its salt may be used. The salts include, for example, sodium salt, potassium salt, lithium salt, and calcium salt, etc. An amount of phenylpyruvic acid or salt thereof in the reaction medium is not critical, but is preferably about 1 to 500 g/l depending on the concentration of the enzyme. When the substrate is used in a lower concentration, it can be used as free acid, and when used in a relatively high concentration, it is preferably used as a salt to simplify the adjustment of the pH of a reaction medium. The sodium salt of phenylpyruvic acids in a high concentration is not dissolved, but the presence of a solid salt in the reaction medium is not disadvantageous. When an ammonium salt of phenylpyruvic acid is used, the ammonium salt may act as a source of ammonium ion as well as a source of phenylpyruvic acid. In the batch-wise reaction, phenylpyruvic acid or salt thereof may be added to the reaction medium at one time at the start of the reaction, or added in portions or continuously during the reaction. The salts of phenylpyruvic acid may be those commercially available or those prepared by neutralization of phenylpyruvic acid with a corresponding base, such as sodium hydroxide or ammonia.

As a source of ammonium ion, an ammonium salt, such as ammonium chloride or ammonium sulfate may be used. Moreover, ammonia gas or a aqueous ammonium hydroxide may be introduced in the reaction medium to maintain the pH value within a predetermined range. As described above, when an ammonium salt of phenylpyruvate acid is used as a substrate, the salt also serves as a source of ammonium ion. The amount of ammonium ion used is stoichiometric or more, in relation to the mol amount of phenylpyruvic acid used, and more specifically, about 1 to 100 mol amount in relation to the mol amount of phenylpyruvic acid used. By increasing the amount of ammonium salt used, the equilibrium of the enzyme reaction involved is forced to the side of L-phenylalanine formation, resulting in an increase in the yield of L-phenylalanine in relation to phenylpyruvic acid.

NADH may be used in an equivalent amount with phenylpyruvic acid. Since NADH is very expensive, however, from the industrial point of view, in addition to the reaction system wherein phenylpyruvic acid is reductively aminated with $NH_4^+$ and NADH to form L-phenylalanine and $NAD^+$, an NADH regenerating system wherein the formed $NAD^+$ is re-reduced to NADH is preferably used. As such an NADH regenerating system, a combination of an enzyme which converts $NAD^+$ to NADH and a substrate for the reaction, for example, a combination of formate dehydrogenase (EC 1.2.1.2) and formate, L-glutamate dehydrogenase (EC 1.4.1.2) and L-glutamate, alcohol dehydrogenase (EC 1.1.1.1) and ethanol, aldehyde dehydrogenase (EC 1.2.1.3) and acetaldehyde, or a combination of glucose-6-phosphate dehydrogenase (EC 1.1.1.49) and glucose-6-phosphate may be used. Moreover, the reduction of $NAD^+$ to NADH with hydrogenase (EC 1.18.3.1) using molecular hydrogen as an electron donor or the reduction of $NAD^+$ to NADH accompanied by the oxidation of methylbiologen or dihydrolipoamide with diaphorase (EC 1.6.4.3) may be used. Where formate dehydrogenase and formate are used, simultaneously with the reduction of $NAD^+$ to NADH, formic acid is oxidized to carbon dioxide gas, which is easily eliminated from the reaction system, with the result that the equilibrium of the reaction is forced in the desired direction. Therefore, as the NADH regenerating system, the combination of formate dehydrogenase and formate is especially preferable.

Formate dehydrogenase is commercially available, or prepared from *Candida boidinii* No. 2201 (AKU 4705) or *Hansenula polymorpha* ATCC 26012 according to a known procedure described by Kato et al., *Agricultural and Biological Chemistry*, 38, 111–116 (1974). Where formate dehydrogenase is used in the form of cells containing the same, the treatment of the cells can be carried out according to a known procedure described by Izumi et al. in *Journal of Fermentation Technology*, 61, 135–142 (1983).

The concentration of the enzyme for the NADH regenerating system varies, depending on the concentration of the phenylalanine dehydrogenase, etc., and is generally a concentration at which $NAD^+$ is reduced to NADH at a rate corresponding to a rate at which an α-ketocarboxylic acid is reductively aminated, i.e., $NAD^+$ is formed For example, where formate dehydrogenase is used as an enzyme for the NADH regenerating system in combination with 10 to 10,000 units/l of phenylalanine dehydrogenase, the concentration of the formate dehydrogenase is preferably about 10 to 10,000 units/l. As a substrate for formate dehydrogenase, a salt of formic acid, such as sodium formate, potassium formate or ammonium formate is conveniently used. The amount of formate is preferably a one to two equivalent amount of the α-ketocarboxylate used. Where the NADH regenerating system is used, $NAD^+$ or NADH may be added to 0.1 to 10 mM, which is a usual physiological concentration.

As a reaction medium water or various kinds of an aqueous solution, for example, an aqueous buffer solution, or an aqueous solution containing an organic solvent such as acetone, acetonitrile, dimethylsulfoxide or dimethylformamide may be used. The buffer solutions include Tris-HCl buffer, glycine-NaOH buffer, etc.

Where the NADH regenerating system is not used, reaction is carried out at a pH suitable for the reductive amination of phenylpyruvic acid by the phenylalanine dehydrogenase used. Phenylalanine dehydrogenase derived from Sporosarcina is used at a pH of 8 to 10, preferably approximately at a pH of 9, while phenylalanine dehydrogenase derived from Bacillus is used at a pH of 9 to 11, preferably approximately at a pH of 10. Where the NADH regenerating system is used in combination with the reductive amination of phenylpyruvic acid, the pH value of the reaction medium is selected as a value within the range wherein both the reductive amination of α-ketocarboxylic acid and the reduction of $NAD^+$ to NADH proceed satisfactorily. Such a pH range is that where a combination of phenylalanine dehydrogenase from Sporosarcina and formate dehydrogenase from *Candida boidinii* is used, usually a pH of 7.5 to 9.5, preferably a pH of 8.0 to 9.0; while where a combination of phenylalanine dehydrogenase from Bacillus and formate dehydrogenase from *Candida boidinii* is used, the pH range is usually 8 to 10, preferably 8.5 to 9.5.

The reaction temperature is selected under the same consideration as made for the selection of the pH range, and the reaction temperature is usually 20° C. to 50° C., preferably 25° C. to 40° C.

The reaction term is not critical, and is selected so that a substrate phenylpyruvic acid is converted to L-phenylalanine at a satisfactory conversion ratio, depending on the concentration of the substrate and amount of enzymes present in the reaction medium.

The reaction may be carried out batch-wise or continuously.

According to another embodiment of the present process, a substrate phenylpyruvic acid is converted to L-phenylalanine, in the presence of a growing culture such as a medium containing living cells, living cells separated from cultured broth, cells treated to an extent wherein an enzyme system necessary for the conversion of phenylpyruvic acid to L-phenylalanine is not destroyed, and in the presence of an energy source, without the artificial addition of NADH, $NAD^+$, and the NADH regeneration system. The energy source is added to a reaction medium, and the energy source may act as an electron donor for a reductive amination of phenylpyruvic acid. The energy sources include, for example, sugars such as arabinose, ribose, ribulose, xylose, fucose, rhamnose, fructose, galactose, gluconate, trehalose, glucose, mannitol, mannose, sorbitol, sorbose, inositol, lactose, maltose, sucrose, raffinose, glycerine, starches, inulin, glycogen, carboxymethylcellulose, and the like. Further, the energy sources include alcohols such as ethanol and methanol, organic acids such as propionic acid, acetic acid, formic acid, citric acid, pyruvic acid, succinic acid, malic acid, α-keto-glutaric acid, and the like.

For the second embodiment, the reaction medium, reaction pH, reaction temperature, and other conditions are selected as described for the first embodiment. The second embodiment also does not require the aerobic condition.

L-phenylalanine thus formed is recovered and purified according to any conventional procedure. For example, the reaction mixture is added to trichloroacetic acid to precipitate protein, and the precipitate, if any, as well as the cells, is eliminated by filtration or centrifugation to obtain a filtrate or supernatant containing the L-phenyl alanine. The product in the filtrate or supernatant is then purified by, for example, ion exchange resin, and finally crystallized.

A quantitative analysis of L-phenylalanine is carried out by bioassay using, for example, *Leuconostoc mesenteroides* ATCC 8042, or by paper chromatography wherein a sample containing L-amino acid is separated in filter paper, a spot of L-phenylalanine is developed with ninhydrin, and the developed spot is eluted for spectro-photometric analysis.

EXAMPLES

The present invention will now be further illustrated by, but is by no means limited to, the following examples.

EXAMPLE 1.

Preparation of chromosomal DNA containing phenylalanine dehydrogenase gene (1)

*Bacillus sphaericus* SCRC-R79a (FERM BP-1013) was inoculated into 3 l of a medium containing 2 g/l of L-phenylalanine, 5 g/l of yeast extract, 10 g/l of peptone, 2 g/l of $K_2HPO_4$, 1 g/l of NaCl and 0.5 g/l of $MgSO_4 \cdot 7H_2O$, pH 7.0), and cultured therein for about 10 hours at 30° C., with shaking, to a cell concentration of $OD_{616}=1.1$, which value has been previously confirmed to correspond to the logarithmic growth phase.

The cultured product was centrifuged to collect cells, and 10 g of the wet cells was used to extract chromosomal DNA according to the Doi method (see, literature 1). Namely, the cells were suspended in 40 ml of a TEN buffer (10 mM Tris-HCl, pH 6.7, 1 mM EDTA, and 10 mM NaCl), and the suspension was centrifuged to collect the cells. The precipitated cells were suspended in 20 ml of a SET buffer (20% sucrose, 50 mM Tris-HCl, pH 7.6, and 50 mM EDTA), 10 mg of lysozyme was added to the suspension, and the whole was incubated at 37° C. for 30 minutes. After the formation of spherophasts was confirmed under a microscope, 10 ml of a TEN buffer and 0.25 g of sodium dodecyl sulfate was added to the above-mentioned suspension to lyze the spherophasts The lysate was extracted with phenol/chloroform in a conventional manner followed by an ethanol precipitation of DNA, which was then picked up with a glass bar. The DNA was dissolved in 10 ml of a TEN buffer, 0.5 mg of RNase was added to the solution, and the whole was incubated at 37° C. for two hours. 1 mg of pronase was added to the solution, which was then incubated at 37° C. for one hour.

After phenol/chloroform extraction, DNA was precipitated with ethanol and dried under a reduced pressure. The dried DNA was dissolved in a TEN buffer.

EXAMPLE 2.

Insertion of chromosomal DNA into vector (1)

Plasmid pUC9 or pBR322 was used as a vector, and accordingly, 10 μg of pUC9 or pBR322 was digested with a restriction endonuclease Hind III at 37° C. for two hours, treated with calf thymus phosphatase at 37° C. for one hour, and then treated with phenol.

The thus-treated solution was subjected to agarose (1%) electrophoresis, and a 2.7 kb DNA fragment from the pUC9 or a 4.4 kb DNA fragment from the pBR322 was isolated by electroelution. The elute was extracted with phenol/chloroform followed by ethanol precipitation of a vector DNA, which was then dissolved in 20 μl of sterile water.

On the other hand, 50 μg of chromosomal DNA prepared in Example 1 was digested with 50 units of Hind III at 37° C. for 16 hours, treated with phenol/chloroform, and precipitated with ethanol. The precipitated DNA was then dissolved in 50 μl of sterile water, and 0.5 μg of the vector DNA and 2 μg of the chromosomal DNA, prepared as above, were mixed and ligated using a T4 DNA ligase in the presence of ATP and dithiothreitol at 12.5° C. for 16 hours.

The reaction mixture was used to transform *E. coli* according to a conventional procedure. The host used was *E. coli* K-12/JM103 for the vector pUC9, and *E. coli* K-12/PR1 for the vector pBR322.

EXAMPLE 3.

Screening of phenylalanine dehydro genase positive clone

The transformation mixture was plated on nitrocellulose filters put on LB plate supplemented with 50 μg/ml ampicillin at a ratio of 500 to 1000 clones per filter. After culturing at 37° C. for 16 hours, the culture was replicated on fresh nitrocellulose filters, which were then incubated at 37° C. for three hours.

The nitrocellulose filter was soaked in a lysozyme solution (5 mg/ml lysozyme, 10 mM Tris-HCl, pH 7.5, and 1 mM EDTA) and allowed to stand at a room temperature for several tens of minutes to lyse the *E. coli* cells. The filter was then soaked in 0.5 ml of a tetrazolium solution (0.2 M Tris-HCl, pH 8.5, 1.5 mM $NAD^+$, 0.8 mM 2-p-iodophenyl-3-p-nitrophenyl-5-phenyltetrazoliumchloride and 0.32 mM phenazine methosulfate), and transformants providing a deep reddish violet color were selected.

As a result, about 2000 each of ampicillin resistant transformants from vectors pUC9 and pBR322 provided one phenylalanine dehydrogenase positive clone respectively.

EXAMPLE 4.

Analysis of plasmid from transformant

Plasmids were extracted from phenylalanine dehydrogenase positive clones, and a recombinant plasmid derived from pUC9 as a vector was designated as pBPDH1 Each plasmid was cleaved to prepare a restriction endonuclease cleavage map thereof. The map is set forth in FIG. 1.

A nucleotide sequence of a DNA fragment containing a region coding for phenylalanine dehydrogenase in the plasmid pBPDH1, and an amino acid sequence corresponding to the nucleotide sequence, are set forth in FIGS. 3-1 to 3-3. This sequence is also present in plasmids pBPDH1-A as pBPDH1-BS, as well as other plasmids of the present invention shown in FIGS. 1 and 2.

EXAMPLE 5.

Subcloning of pBPDH1 (FIG. 1)

In this example, 10 μg of plasmid pBPDH1 was digested with Hind III, the digestion product was subjected to agarose gel (0.7%) electrophoresis, and a DNA fragment of about 8 kb was isolated by electroelution. Then, 2 μg of pUC9 was digested with Hind III and treated with calf thymus phosphatase followed by phenol/chloroform. Both reaction mixtures were mixed, purified by Elutip-d column (Schleicher & Schuell), and the DNA was precipitated with ethanol.

The precipitate was then dissolved in a T4 ligase buffer (50 mM Tris-HCl, pH 7.4, 10 mM MgCl$_2$, 10 mM DTT, and 1 mM ATP), and ligation was carried out using T4 ligase.

The reaction mixture was used to transform E. coli JM103. clone showed as a white color on an LB plate containing 50 μg/ml ampicillin, 0.3 mM isopropyl-B-D-thiogalactoside, and 0.03% 5-bromo-4-chloro-3-indoryl-8-D-galactoside, which indicates a lack of β-galactosidase activity. A plasmid was extracted from these clones, and a recombinant plasmid wherein a Hind III fragment of about 6 kb was inserted in the Hind III site of pUC9 was selected. The recombinant plasmid was designated as pBPDH1-A.

EXAMPLE 6.

Construction of plasmid pBPDH3 (FIG. 1)

In this example, 2 μg of pBR322 was digested with Hind III, treated with calf thymus phosphatase, followed by phenol/chloroform. To the treated product was added the DNA fragment of about 6 kb isolated in Example 5, and the DNA mixture was purified by Elutip-d column and precipitated with ethanol. The precipitate was dissolved in 10 μl of a T4 ligase buffer (50 mM Tris-HCl, pH 7.4, 10 mM MgCl$_2$, 10 mM DTT and 1 mM ATP), and ligation was carried using a T4 ligase. The reaction mixture was used to transform E. coli RR1. The transformants were screened according to a conventional procedure, and a plasmid pBPDH3 was obtained.

EXAMPLE 7

Subcloning of pBPDH1-A (FIG. 1)

In this example, 10 μg of pBPDH1-A was digested with Bam HI and Sal I, the digest was subjected to agarose gel (0.7%) electrophoresis, and a DNA fragment of about 3 kb was isolated by electroelution Then, 2 μg of pUC9 was digested with Bam HI and Sal I, and treated with calf thymus phosphatase, followed by phenol/chloroform. According to the same procedure as described in Example 5, both reaction mixtures were mixed, and after purification by Elutip-d column, DNA was ligated using a T4 ligase, and the reaction mixture was used to transform E. coli JM103. Ampicillin resistant transformants were screened according to the same procedure as described in Example 5 to select white clones which do not exhibit β-galactosidase activity. Plasmids were extracted from these clones, and on the basis of restriction enzyme digestion patterns, a recombinant plasmid wherein a Bam HI - Sal I fragment of about 3.2 kb was inserted in the Bam HI - Sal I sites of pUC9 was selected and designated as pBPDH1-BS. The nucleotide sequence of a DNA fragment in the plasmid pBPDH1-BS containing a region coding for phenylalanine dehydrogenase, and a corresponding amino acid sequence, are set forth in FIGS. 3-1 to 3-3. The nucleotide sequence was determined according to a dideoxy chain termination method (literature 4).

EXAMPLE 8.

Figure 2:
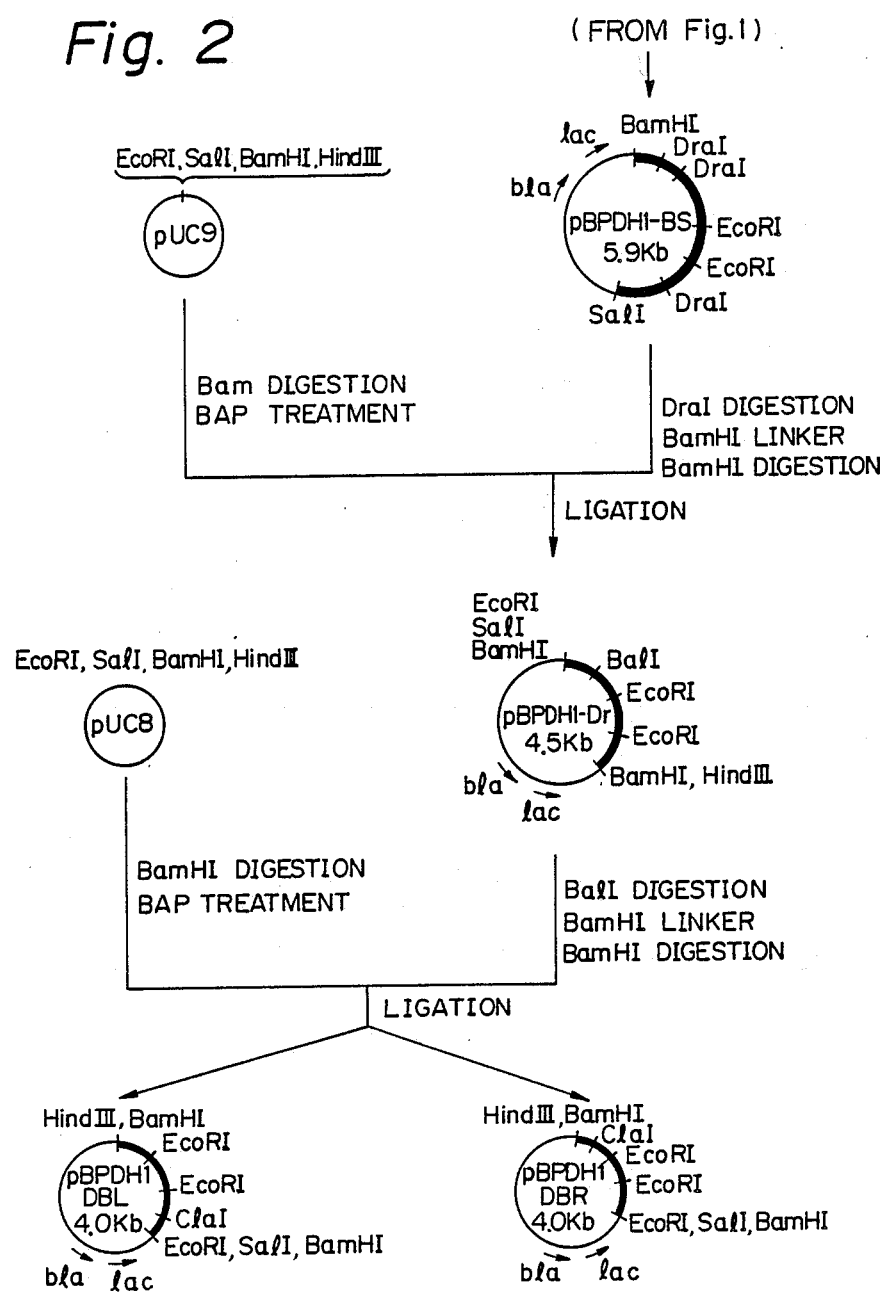

Subcloning of pBPDH1-BS (FIG. 2)

In this example, 10 μg of pBPDH1-BS was digested with Dra I, and the digested DNA was precipitated with ethanol. The Dra I-digested DNA and 0.01 OD$_{260}$ units of a Bam HI linker phosphorylated at the 5' end thereof were ligated in 20 μl of a T4 ligase buffer using 350 units of a T4 ligase at 22° C. for 5 hours, and the ligated DNA was precipitated with ethanol. The thus-prepared DNA was digested with Bam HI, the digest was subjected to agarose gel (0.7%) electrophoresis, and a DNA fragment of about 2 kb was isolated by electroelution.

On the other hand, 2 μg of pUC9 was digested with Bam HI, treated with calf thymus phosphatase, followed by phenol/chloroform. According to the same procedure as described in Example 5, both reaction mixtures were mixed, purified by Elutip-d column, and ligated using a T4 ligase The reaction mixture was used to transform E. coli JM109. According to the same procedure as described in Example 5, β-galactosidase negative clones were selected.

Plasmids were extracted from these clones, and on the basis of the restriction enzyme digestion pattern, a recombinant plasmid wherein a DNA fragment of about 1.8 kb was inserted in the Bam HI site of pUC9 was selected and designated as pBPDH1-Dr.

EXAMPLE 9.

Subcloning of pBPDH1-Dr (FIG. 2)

In this example, 10 μg of pBPDH1-Dr was digested with Bal I and precipitated with ethanol. The Bal I-digested DNA and 0.01 OD$_{260}$ units of a Bam HI linker phosphorylated at the 5' end thereof were ligated in 10 μl of a ligase buffer using 350 units of a T4 ligase at 16° C. for 6 hours, and the ligated DNA was precipitated with ethanol. The DNA was digested with Bam HI, the digest was subjected to agarose gel (0.7%) electrophoresis, and a DNA fragment was isolated by electroelution. The elute was treated three times with phenol/chloroform, and DNA was precipitated with ethanol.

On the other hand, 2 μg of pUC8 was digested with Bam HI, and treated with calf thymus phosphatase, followed by phenol/chloroform, and the digested DNA was precipitated with ethanol.

Both the reaction mixtures, prepared as described above were ligated using a T4 ligase, and the reaction mixture was used to transform E. coli JM109. According to the same procedure as described in Example 5, clones which did not exhibit β-galactosidase activity were selected. Plasmids were extracted from these clones, and on the basis of the restriction endonuclease digestion pattern, two recombinant plasmids wherein a DNA fragment of about 1.3 kb was inserted in the Bam HI site of pUC8 were selected and designated as pBPDH1-DBL and pBPDH1-DBR, respectively. These plasmids are different in the orientation of the DNA fragment inserted therein.

E. coli transformants containing the plasmid thus obtained exhibit phenylalanine dehydrogenase activity.

*Escherichia coli* JM109/pBPDH1-DBL containing the plasmid pBPDH1-DBL was deposited with the FRI as FERM P-8873 on July 24, 1986; and *Escherichia coli* JM109/pBPDH1-DBR containing the plasmid pBPDH1-DBR was deposited with the FRI as FERM P-8794 on June 3, 1986.

EXAMPLE 10.

Production of phenylalanine dehydrogenase using transformant containing recombinant plasmid (1)

*E. coli* JM103/pBPDH1 containing the plasmid pBPDH1, *E. coli* RR1/pBPDH3 containing the plasmid pBPDH3, and *E. coli* JM103/pBPDH1-DBL containing the plasmid pBPDH1-DBL were tested to determine their ability to produce phenylalanine dehydrogenase.

The above-mentioned transformant *E. coli* were cultured in 140 ml of LB medium containing 50 μg/ml of ampicillin at 37° C. for 6 hours. As a control, *Bacillus sphaericus* SCRC-R79a was cultured in 140 ml of a medium containing 0.1% of L-phenylalanine, 1% of peptone, 0.5% of yeast extract, 0.2% of $K_2HPO_4$, 0.1% of NaCl, and 0.02% of $MgSO_4 \cdot 7H_2O$ (pH 7.0) at 37° C. overnight.

For each culture, cultured cells were collected by centrifugation, and the cells were washed with 70 ml of a 0.85% NaCl solution. After the cells were suspended in 10 ml of 0.1 M potassium phosphate buffer (pH 7.0), the suspension was ultra-sonicated at 2° C., 200 W, for 20 minutes. The sonicate was dialyzed in 10 l of a 0.01 M potassium phosphate buffer (pH 7.0) at 4° C. overnight. The dialyzate was assayed to determine the phenylalanine dehydrogenase activity according to the above-mentioned procedure. The results are set forth in Table 1.

TABLE 1

| Producer | Enzyme activity (units/1 l culture) |
|---|---|
| B. sphaericus SCRC-R79a | about 60 |
| E. coli JM103/pBPDH1 | 1500 |
| E. coli RR1/pBPDH3 | 2600 |
| E. coli JH103/pBPDH1-DBL | 3000 |

As seen from Table 1, *E. coli* transformed with a plasmid of the present invention produced 25 to 50 times as much phenylalanine dehydrogenase compared with that produced by *B. sphaericus*.

EXAMPLE 11.

Synthesis of L-phenylalanine (1)

L-phenylalanine was synthesized using cells of *E. coli* RR1 containing the plasmid pBPDH3. As an NADH regeneration system, enzymes for glycolysis in *E. coli* were used. The above-mentioned *E. coli* was inoculated in an LB medium containing 50 μg/ml of ampicillin at a ratio of 1%, and cultured at 37° C. for 6 hours. The 5 ml of the cultured broth was centrifuged to collect cells, which were then washed with a 0.85% NaCl solution. The cells were suspended in 3 ml of a reaction mixture containing 200 μ moles of an $NH_4Cl-NH_4OH$ buffer (pH 9.0), 109 μ moles of a sodium phenylpyruvate, and 267 μ moles of a lactose, and the suspension was allowed to stand at 30° C. for 24 hours. As a result, 20 mg/ml (yield 33%) of L-phenylalanine was accumulated, as determined by the above-mentioned L-phenylalanine assay procedure.

EXAMPLE 12.

Synthesis of L-phenylalanine (2)

In this example, as an NADH regeneration system, cells of *Candida boidinii* No. 2201 containing formate dehydrogenase were used. *Candida boidinii* No. 2201 was cultured according to the Tani method (literature 2), and cells of *C. boidinii* and cells of *E. coli* RR1/pBPDH3 containing the plasmid pBPDH3 cultured as above were separately treated with acetone (literature 3). Then, 15 mg of the acetone-treated cells of *E. coli* corresponding to 6.3 ml of the cultured broth having 6.3 units of phenylalanine dehydrogenase activity, and 30 mg of the acetone-treated *C. boidinii* cells were suspended in 3 ml of a reaction mixture containing 250 μ moles of a Tris-HCl buffer (pH 8.2), 728 μ moles (0.136 g) of a phenylpyruvic acid, 2 m moles (0.122 g) of an ammonium formate, and 25 μ moles (1.8 g) of $NAD^+$, and the suspension was allowed to stand for 30° C. for 53 hours to synthesize L-phenylalanine. As a result, 0.126 g (42 mg/ml) of L-phenylalanine was obtained. This yield corresponds to a 100% conversion.

EXAMPLE 13.

Preparation of chromosomal DNA (2)

According to the method of Doi et al. (literature 1), chromosomal DNA was prepared from *Sporosarcina ureae* SCRC-R04 (FERM BP-1012).

Then, 1 l of a medium containing 1% of L-phenylalanine, 0.5% of yeast extract, 1.0% of peptone, 0.2% of $KH_2PO_4$, 0.1% of NaCl, and 0.02% of $MgSO_4 \cdot 7H_2O$ was autoclaved, and the above-mentioned microorganism was inoculated into the medium and cultured at 30° C. overnight.

The cultured broth was centrifuged to collect cells, which were then suspended in 20 ml of a TEN buffer. The suspension was again centrifuged to collect the cells, which were then resuspended. To the suspension was added 1 ml of 5 mg/ml lysozyme, and the whole was shaken for 30 minutes at 37° C. The mixture was centrifuged to obtain a precipitate, which was then suspended in 5 ml of a TEN buffer. To the suspension were added 0.5 ml of a 25% sodium dodecyl sulfate, 1 ml of a 5 M NaCl and 10 ml of phenol saturated with water to extract DNA. The mixture was centrifuged to obtain a supernatant, and the supernatant was washed with chloroform/isoamylalcohol (24:1, v/v). The whole was then centrifuged, and the supernatant was slowly added to 50 ml of ethanol to precipitate DNA, which was then recovered. After drying the DNA, the DNA was dissolved in a TEN buffer.

EXAMPLE 14.

Preparation of chromosomal DNA library (2)

The 50 μg of chromosomal DNA prepared in Example 13 was digested with 20 units of a restriction endonuclease Eco RI at 37° C. for 2 hours, the reaction mixture was extracted with phenol/chloroform (1:1 v/v), and 2.5 volumes of ethanol was added to the mixture to precipitate DNA.

On the other hand, 5 μg of the vector plasmid pUC9 was digested with 10 units of the above-mentioned corresponding restriction endonuclease at 37° C. for 2 hours. DNA was recovered as described above.

Then, 0.5 μg of the digested vector plasmid pUC9 and 4 μg of the chromosomal DNA fragment was ligated using a T4 DNA ligase to form recombinant plasmids. The plasmids were then used to transform E. coli K-12/JM103 to construct a chromosomal DNA library. Each library comprised 20,000 to 30,000 transformants.

EXAMPLE 15.

Cloning of phenylalanine dehydrogenase gene (2)

The above-mentioned library was plated on nitrocellulose filters (0.45 μm, TYPE TM-1, Toyo Roshi, Japan) put on an LB agar Plate containing 50 μg/ml of ampicillin at a ratio of 1,000 to 2,000 colonies per filter, and incubated at 37° C. for 8 hours. Each filter was replicated to two nitrocellulose filters, and culturing was continued. The latter nitrocellulose filter was soaked in 0.5 ml of 4 mg/ml of a lysozyme solution at a room temperature, and then dried at 45° C. for one hour. The filter was then soaked in 0.5 ml of an active staining solution containing 50 mM of L-phenylalanine, 50 mM of Tris-HCl (pH 8), 0.625 mM of NAD+, 0.064 mM of phenazine methosulfate (PMS), and 0.24 M of nitroblue tetrazalium (INT) at a room temperature for 1 to 5 minutes to select reddish brown-stained colonies (literature 5). Some of the selected colonies were separately cultured in an LB medium containing 50 μg/ml of ampicillin at 37° C. overnight, and the cultured cells were sonicated. The sonicate was then centrifuged to obtain a cell-free extract, and to the extract was added the above-mentioned active staining solution to detect enzyme activity. As a result, a transformant E. coli JM103/pSPDH1 was obtained. A plasmid pSPDH1 contained the phenylalanine dehydrogenase gene.

EXAMPLE 16.

Preparation of restriction endonuclease map and subcloning (2)

Figure 4:
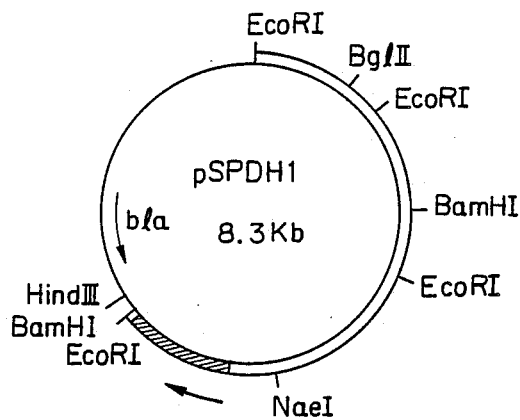
FIG. 4 represents restriction endonuclease cleavage maps for plasmids pSPDH1 and pSPDH2.
Figure 4:
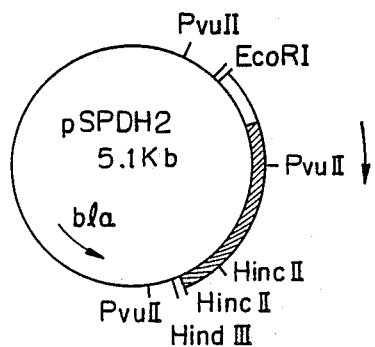

The transformant E. coli JM103/pSPDH1 was cultured in 200 ml of an LB medium containing 50 μg/ml of ampicillin at 37° C. overnight, and according to method of Birnboim and Doly (literature 6), 150 μg of plasmid DNA was obtained. The plasmid pSPDH1 DNA thus obtained was digested with a restriction endonuclease Bam HI, Eco RI, Bgl II, Pvu II, Nae I, Hinc II or the like to prepare a restriction endonuclease map (FIG. 4A).

An insert DNA of about 5.6 kb in pSPDH1 was fragmented to prepare a Nae I - Hind III DNA fragment of about 1.4 kb, the DNA was inserted at the Hind III - Sma I site of the vector plasmid pUC19, and the resulting recombinant plasmids were used to transform E. coli K-12/JM103 to obtain transformant E. coli JM103/pSPDH2 capable of producing phenylalanine dehydrogenase. The restriction endonuclease map of pSPDH2 is set forth in FIG. 4-B.

The nucleotide sequence of the DNA fragment containing a region coding for phenylalanine dehydrogenase in plasmids pSPDH1 and pSPDH2, as well as an amino acid sequence corresponding to the nucleotide sequence, are set forth in FIGS. 5-1 to 5-3. The nucleotide sequence was determined by a dideoxy method (literature 4) and MB dideoxy chain termination method (literature 7).

The transformant Escherichia coli JM103/pSPDH2 was deposited with the FRI as FERM P-8793 in June 3, 1986.

EXAMPLE 17.

-Production of phenylalanine dehydrogenase (2)

E. coli JM103/pSPDH2 and JM103/pSPDH1 were cultured in an LB medium containing 50 μg/ml of ampicillin at 37° C. for 6 hours. On the other hand, as a control, Sporosarcina ureae SCRC-R04 was cultured in the medium described in Example 1 at 30° C. for 16 hours. Each cultured broth was centrifuged to collect cells, which were then suspended in a 0.1 M potassium phosphate buffer (pH 7.0) containing 0.1 mM EDTA and 5 mM of 2-mercaptoethanol, and sonicated. The sonicate was centrifuged, and the supernatant was dialyzed in a 10 mM potassium phosphate buffer (pH 7.0) containing 0.1 M of EDTA and 5 mM of 2-mercaptoethanol at 4° C. overnight. These preparations were assayed according to the above-mentioned method, and the results are set forth in Table 2.

TABLE 2

| Producer | Enzyme activity units/1 l culture |
|---|---|
| S. ureae CSRC-R04 | 60 |
| E. coli JM103/pSPDH1 | 175 |
| E. coli JM103/pSPDH2 | 340 |

As seen from Table 2, recombinant E. coli of the present invention produced 6 times as much phenylalanine dehydrogenase compared to that produced by a wild strain of S. ureae.

EXAMPLE 18.

Synthesis of L-phenylalanine (3)

E. coli JM103/pSPDH2 was cultured according to the same procedure as described in Example 17. On the other hand, Candida boidinii No. 2201 was cultured according to the Tani method (literature 2) to prepare an NADH regeneration system. Each cultured broth was centrifuged to collect cells, which were then treated with acetone (literature 3) to prepare 0.48 g/l of acetone-treated dry cells and 1.3 g/l of acetone-treated dry cells from the E. coli and C. boidinii respectively.

Then, 3 ml of a reaction mixture containing 0.136 g (728 μ moles) of sodium phenylpyruvate, 0.122 g (2 m moles) of ammonium formate, 1.8 mg (2.5 μ moles) of NAD+, 250 m moles of Tris-HCl (pH 8.5), 15 mg of the acetone-treated E. coli cells (corresponding to 30 ml of culture, 6 units of phenylalanine dehydrogenase), and 3 mg of the acetone-treated C. boidinii cells (corresponding to 2.3 ml of culture, 0.14 units of formate dehydrogenase) was incubated at 30° C. for 53 hours. Accordingly, 0.120 g (yield 100%) of L-phenylalanine was obtained.

EXAMPLE 19.

Preparation of chromosomal DNA (3)

A chromosomal DNA was prepared from Bacillus badius IAM 11059 (FERM P-8529) according to the method of Doi et al (literature 1).

That is, the above-mentioned strain was cultured in 1.2 l of a medium containing 1% of L-phenylalanine, 0.5% of yeast extract, 1.0% of peptone, 0.2% of K₂HPO₄, and 0.02% of MgSO₄·H₂O (pH 7.0) at 30° C. for 6 hours. Extraction of the chromosomal DNA was carried out according to the same procedure as described in Example 1.

EXAMPLE 20.

Preparation of chromosomal DNA library (3)

Next, 50 μg of the chromosomal DNA prepared in Example 19 was digested with 300 units of restriction endonuclease Eco RI at 37° C. overnight, the digest was extracted with phenol/chloroform (1:1, v/v), and DNA was precipitated with 2 volumes of ethanol. On the other hand, 10 μg of the vector plasmid pUC19 was digested with 60 units of Eco RI at 37° C. overnight, and DNA was recovered in the same manner as described above.

Then, 0.5 μg of the Eco RI-digested vector plasmid pUC19 and 1 μg of the Eco RI-digested chromosomal DNA were ligated using DNA ligase, and the reaction mixture was used to transform E. coli K-12/JM103 and prepare a chromosomal DNA library. This chromosomal DNA library comprised 23,000 transformants.

EXAMPLE 21.

Cloning of phenylalanine dehydrogenase gene (3)

The above-mentioned transformants were plated on nitrocellulose filters put on an LB agar plate containing 50 μg/ml of ampicillin at a ratio of 1000 to 2000 colonies per nitrocellulose filter, and then cultured. After about 10 hours, colonies on the nitrocellulose were replicated onto fresh nitrocellulose filters, and culturing was continued. The latter nitrocellulose filter was soaked in 1.0 ml of a 4 mg/ml lysozyme aqueous solution at 30° C. for 10 minutes, followed by 10 ml of a 0.1 M Tris-HCl (pH 8.0) at 50° C. for 10 minutes. The nitrocellulose filters were soaked in 1.0 ml of an active staining solution containing 50 mM of Tris-HCl (pH 8.0), 0.625 mM of $NAD^+$, 0.065 mM of PMS, and 0.24 mM of INT at a room temperature for 1 to 5 minutes, and the colonies stained to a reddish violet color were selected (literature 5). From about 23,000 transformants was obtained about 50 transformants exhibiting an activity. Among these transformants, 12 transformants were separately cultured in 1 l of an LB medium containing 50 μg/ml ampicillin, and according to the method of Birnboim and Doly (literature 6) a plasmid DNA was prepared from each culture. These plasmid DNA's were analyzed to determine the gene size thereof, using agarose gel. As a result, it was determined that one clone had a gene fragment of about 7 kb inserted therein, and 11 clones had a gene fragment of about 3.8 kb inserted therein. All of these transformants exhibited phenylalanine dehydrogenase activity. Among these transformants, a transformant containing a plasmid having the 3.8 kb gene fragment was designated as E. coli JM103/pBBPDH19.

EXAMPLE 22.

Preparation of restriction endonuclease map (3)

Figure 6:
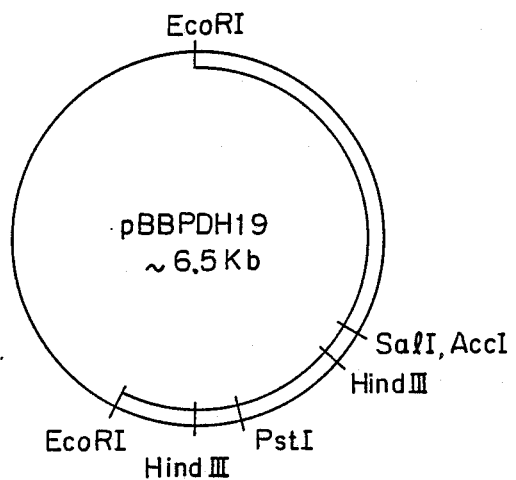
FIG. 6 represents a restriction endonuclease cleavage map for the plasmid pBBPDH19.

The transformant E. coli JM101/pBBPDH19 was cultured in 1 l of an LB medium containing 50 μg/ml of ampicillin at 37° C. overnight, and according to the method of Birnboim and Doly (literature 6), about 150 μg of a plasmid DNA was prepared. The plasmid pBBPDH19 DNA was separately digested with a restriction endonuclease Sma I, Xma I, Bam HI, Eco RI, Hind III, Pst I, Sal I, Acc I, and the like, to prepare a restriction endonuclease map (FIG. 6).

The transformant E. coli JM103/pBBPDH19 was cultured and the plasmid pBBPDH19 was isolated as above. This plasmid was used to transform E. coli RR1 to obtain a transformant Escherichia coli RR1/pBBPDH19, which was deposited with the FRI as FERM P-8890 on Aug. 7, 1986.

EXAMPLE 23.

Production of phenylalanine dehydrogenase (3)

E. coli RR1/pBBPDH19 was cultured in an LB medium containing 50 μg/ml ampicillin at 37° C. for 12 hours. On the other hand, Bacillus badius IAM 11059 (FERM P-8529) as a control was cultured in the medium described in Example 1 at 30° C. for 20 hours. Each cultured broth was centrifuged to collect cells, which were then suspended in 0.1 M of a potassium phosphate buffer containing 0.1 mM EDTA and 5 mM 2-mercaptoethanol, sonicated, the sonicate was centrifuged, and the supernatant was dialyzed in a 10 mM potassium phosphate buffer containing 0.1 mM of EDTA and 5 mM of 2-mercaptoethanol, overnight. These cell-free extracts were assayed to determine the phenylalanine dehydrogenase activity thereof, according to the above-mentioned procedure. The results are set forth in Table 3.

TABLE 3

| Producer | Enzyme activity (units/1 l culture) |
|---|---|
| B. badius IAM 11059 | 1,090 |
| E. coli RR1/pBBPDH19 | 6,900 |

As seen from Table 3, E. coli containing the recombinant plasmid of the present invention exhibited an phenylalanine dehydrogenase activity that was about 6 to 7 times greater than that of a wild Bacillus badium strain.

EXAMPLE 24.

Purification of phenylalanine dehydrogenase from E. coli RR1/pBBPDH19

E. coli RR1/pBBPDH19 was cultured in 1.8 l of an LB medium containing 50 μg/ml of ampicillin at 37° C. for 12 hours. The cultured broth was centrifuged to collect cells, which were then washed with a physiological saline, and suspended in 1 l of a 0.1 M phosphate buffer (pH 7.0) containing 0.1 mM EDTA and 5 mM 2-mercaptoethanol. The suspension was sonicated at 9 kHz for one hour to disrupt the cells, and the sonicate was centrifuged at 14,000 xg for 20 minutes to eliminate cell debris, so that a crude cell-free extract containing phenylalanine dehydrogenase was obtained. After the cell-free extract was heated at 50° C. for 10 minutes, a solid ammonium sulfate was added to the cell-free extract to a concentration of 30% ammonium sulfate saturation. The whole was stirred for 30 minutes to allow the formation of a precipitate, and centrifuged at 14,000 xg for 20 minutes to eliminate the precipitate. Solid ammonium sulfate was added to the supernatant to a 60% ammonium sulfate saturation. The whole was then centrifuged at 14,000 xg for 20 minutes to recover a precipitate containing enzyme activity, and the precipitate was dissolved in a small volume of a 0.01 M phosphate buffer (pH 7.0), and the resultant solution was dialyzed in a 0.01 M phosphate buffer (pH 7.0) containing 0.1 mM of EDTA and 5 mM of 2-mercaptoethanol. This enzyme solution was applied to a DEAE-Toyopearl 650 M column previously equilibrated with a 0.01 M phosphate buffer (pH 7.0) containing 0.1 mM of EDTA and 5 mM of 2-mercaptoethanol, and the elution was carried out using a 0.1 M phosphate buffer (pH 7.0)

containing 0.1 mM of EDTA and 5 mM of 2-mercaptoethanol.

Active fractions were then combined and dialyzed, and the dialyzate was concentrated and subjected to gel filtration chromatography using Sephadex G-200 equilibrated with a 0.05 M phosphate buffer (pH 7.0) containing 0.1 mM of EDTA and 5 mM of 2-mercaptoethanol. By this procedure, phenylalanine dehydrogenase was purified to an about 15-fold degree with a yield of about 54%. The specific activity and recovery percentage during this purification procedure are set forth in Table 4. It was confirmed that the final enzyme preparation was homogeneous, as shown by polyacrylamide gel electrophoresis and DS-polyacrylamide gel electrophoresis.

TABLE 4

| Step | Total activity (units) | Total protein (mg) | Specific activity (units/mg) | Recovery (%) |
|---|---|---|---|---|
| 1. Cell-free extract | 12,400 | 1,760 | 7.05 | 100 |
| 2. Heat treatment | 11,900 | 1,310 | 8.78 | 96 |
| 3. Ammonium sulfate fraction | 7,680 | 942 | 7.91 | 62 |
| 4. DEAE-Toyopearl | 7,100 | 299 | 23.7 | 57 |
| 5. Sephadex G-200 | 6,710 | 98.8 | 67.9 | 54 |

EXAMPLE 25.

Synthesis of L-phenylalanine (4)

*E. coli* RR1/pBBPDH19 was cultured as described above. On the other hand, *Candida boidinii* No. 2201 was cultured according to the method of Tani et al. (literature 2) to prepare an NADH regeneration system. Each cultured broth was centrifuged to collect cells, which were then treated with acetone to obtain a 0.5 g/l culture of cetone-treated *E. coli* cells and a 1.3 g/l culture of acetone-treated *C. boidinii* cells.

Then, 3 ml of a reaction mixture containing 0.136 g (728 μ moles) of sodium phenylpyruvate, 0.122 g (2 m moles) of ammonium formate, 1.8 mg (2.5 μ moles) of NAD+, 250 μ moles of Tris-HCl (pH 8.5), 5 mg of acetone-treated *E. coli* cells (corresponding to 10 ml of the culture, 69 units of L-phenylalanine dehydrogenase), and 3 mg of the acetone-treated *C. boidinii* cells (corresponding to 2.3 ml of the culture, 0.14 units of formate dehydrogenase) was incubated at 30° C. for 48 hours. Subsequently, 0.120 g (yield 100%) of L-phenylalanine was obtained.

For the following microorganisms the national depositions were transferred to the international depositions under the Budapest treaty on Aug. 7, 1987:

| strain | National deposition. No. | International deposition No. |
|---|---|---|
| E. coli JM103/pSPDH2 | FERM P-8793 | FERM BP-1435 |
| E. coli JM109/pBPDH1-DBR | FERM P-8794 | FERM BP-1434 |
| E coli JM109/pBPDH1-DBL | FERM P-8873 | FERM BP-1433 |
| E. coli RR1/pBBPDH19 | FERM P-8890 | FERM BP-1436 |

LITERATURE (1) R. L. Rodriguez et al. Recombinant DNA Teqhnique, An Introduction, Addison-Wesley Publishing Company (1983) pp 162.

Y. Tani et al. Agric. Biol. Chem., 36, 68, (1972).

Y. Izumi et al. J. Ferment. Technol., 61, 135 (1983).

H. Hattori et al. Nucl. Acids Res., 13, 7813 (1985).

H. Mollering et al. Methods of Enzymatic Analysis Academic Press, 1, 136–144 (1974).

H. C. Birnboim et al. Nucl. Acids Res., 7, 1513 (1979).

F. Sanger et al. Proc. Natl. Acad. Sci. USA 20 5463 (1977).

What is claimed is:

1. An isolated gene coding for phenylalanine dehydrogenase of a microorganism selected from the group consisting of *Bacillus sphaericus* SCRC-R79a (FERM BP-1013) and *Bacillus badius* IAM 11059 (FERM BP-2757).

2. An isolated gene according to claim 1 wherein the gene comprises the following nucleotide sequence:

```
GCAAAACAGCTTGAAAAGTCATCAAAAATTGGTAATGAGGACGTTTTTCAA
            A K Q L E K S S K I G N E D V F Q
AAAATAGCGAATCACGAGCAGATTGTGTTCTGTAATGATCCGGTATCCGGCCTGCAAGCTATCATT
 K I A N H E Q I V F C N D P V S G L Q A I I
GCTATCCACGATACAACCCTAGGCCCCGCTTTAGGTGGAACTCGCATGTATCCCTATAAAAATGTG
 A I H D T T L G P A L G G T R M Y P Y K N V
GATGAAGCTCTGGAAGATGTGCTTCGCCTGTCAGAAGGAATGACGTATAAATGCGCAGCCGCCGAT
 D E A L E D V L R L S E G M T Y K C A A A D
ATCGATTTCGGCGGCGGGAAGGCGGTCATTATCGGAGATCCAGAAAAGGATAAATCTCCGGCATTG
 I D F G G G K A V I I G D P E K D K S P A L
TTCCGTGCATTTGGTCAATTTGTGGAATCACTGAATGGACGATTTTACACAGGTACTGACATGGGG
 F R A F G Q F V E S L N G R F Y T G T D M G
ACCACGATGGATGATTTTGTCCATGCACAGAAAGAGACGAATTTCATTAACGGAATTCCTGAGCAG
 T T M D D F V H A Q K E T N F I N G I P E Q
TATGGTGGAAGCGGCGACTCGTCGATTCCGACCGCCCAGGGAGTCATTTATGCACTGAAGGCTACA
 Y G G S G D S S I P T A Q G V I Y A L K A T
AACCAGTATTTATTTGGAAGCGATAGCCTTTCAGGTAAAACATATGCTATTCAAGGGCTGGGAAAA
 N Q Y L F G S D S L S G K T Y A I Q G L G K
GTAGGGTATAAAGTAGCGGAACAGCTCTTAAAAGCCGGCGCCGATTTATTTGTAACGGATATACAT
 V G Y K V A E Q L L K A G A D L F V Y D I H
GAAAATGTCCTCAATTCCATTAAGCAAAAATCAGAAGAGCTTGGCGGTTCAGTGACCATTGTAAAA
 E N V L N S I K Q K S E E L G G S V T I V K
AGTGACGATATTTACAGCGTACAAGCGGATATATTTGTTCCGTGTGCGATGGGTGGTATTATCAAT
 S D D I Y S V Q A D I F V P C A M G G I I N
GATAAAACCATTCCTAAGTTAAAGGTGAAGGCTGTTGTGGGATCAGCCAATAACCAGCTCAAAGAC
 D K T I P K L K V K A V V G S A N N Q L K D
CTCCGCCATGCAAATGTACTAAACGAAAAGGGAATTCTATATGCACCCGATTATATCGTCAATGCC
 L R H A N V L N E K G I L Y A P D Y I V N A
GGCGGCTTGATCCAGGTTGCTGACGAACTTTATGGGCCGAATAAAGAGCGGGTCTTGCTCAAAACG
 G G L I Q V A D E L Y G P N K E R V L L K T
AAAGAAATTTACCGTTCTCTGCTTGAAATTTTTAATCAGGCAGCCCTTGACTGCATCACAACAGTG
 K E I Y R S L L E I F N Q A A L D C I T T V
```

```
-continued
GAGGCCGCAAATAGGAAGTGTCAAAAGACGATTGAGGGCCAGCAAACCCGTAATAGTTTCTTTTCT
 E   A   A   N   R   K   C   Q   K   T   I   E   G   Q   Q   T   R   N   S   F   F   S
AGGGGACGCAGGCCGAAGTGGAACATAAAAGAG
 R   G   R   R   P   K   W   N   I   K   E   .
```

3. An expression plasmid containing the gene of claim 1.

4. An expression plasmid according to claim 3, wherein the plasmid is selected from the group consisting of pBPDH1, pBPDH3, pBPDH1-DBL, pBPDH1-DBR, and pBBPDH19.

5. A microorganism transformed with the plasmid of claim 3.

6. A microorganism according to claim 5, wherein the microorganism is *E. coli.*

7. A microorganism according to claim 6, wherein the *E. coli* is selected from the group consisting of *E. coli* JM109/pBPDH1-DBL (FERM P-8873), *E. coli* JM109/pBPDH1-DBR (FERM P-8794), and *E. coli* RR1/pBBPDH19 (FERM P-8890).

8. A process for production of phenylalanine dehydrogenase comprising the steps of:
culturing the microorganism of claim 5, and
recovering the phenylalanine dehydrogenase from the cultured product.

* * * * *